United States Patent
Gross

(10) Patent No.: US 9,591,969 B2
(45) Date of Patent: Mar. 14, 2017

(54) PATIENT POSITIONING DEVICE, AND MEDICAL IMAGING METHOD AND APPARATUS EMPLOYING SAME

(71) Applicant: Patrick Gross, Buckenhof (DE)

(72) Inventor: Patrick Gross, Buckenhof (DE)

(73) Assignee: Siemens Aktiengesellschaft, Munich (DE)

( * ) Notice: Subject to any disclaimer, the term of this patent is extended or adjusted under 35 U.S.C. 154(b) by 144 days.

(21) Appl. No.: 14/039,329

(22) Filed: Sep. 27, 2013

(65) Prior Publication Data

US 2014/0088404 A1   Mar. 27, 2014

(30) Foreign Application Priority Data

Sep. 27, 2012 (DE) ......................... 10 2012 217 634

(51) Int. Cl.
*A61B 5/00* (2006.01)
*A61B 5/055* (2006.01)
*A61B 5/06* (2006.01)

(52) U.S. Cl.
CPC .......... *A61B 5/0035* (2013.01); *A61B 5/0555* (2013.01); *A61B 5/062* (2013.01)

(58) Field of Classification Search
USPC .......................................................... 5/601
See application file for complete search history.

(56) References Cited

U.S. PATENT DOCUMENTS

| 5,398,691 A | * | 3/1995 | Martin et al. ................. 600/463 |
| 6,322,251 B1 | | 11/2001 | Ballhaus et al. |
| 2004/0199072 A1 | * | 10/2004 | Sprouse ................. A61B 34/20 600/424 |
| 2009/0281419 A1 | | 11/2009 | Troesken et al. |

OTHER PUBLICATIONS

"MR-US Fusion for Targeted Prostate Biopsy," Weiss et al., 2010 ISMRM Annual Meeting, Stockholm, Sweden (2010).

* cited by examiner

*Primary Examiner* — Katherine Fernandez
*Assistant Examiner* — Farshad Negarestan
(74) *Attorney, Agent, or Firm* — Schiff Hardin LLP

(57) ABSTRACT

A patient positioning device has an electromagnetically transparent transfer plate for positioning an examination subject, and at least one patient bed. The electromagnetically transparent transfer plate can be disposed on the patient bed for imaging an examination region of the examination subject with a first imaging device. For imaging the examination region of the examination subject with the second imaging device that has an electromagnetic localization device, the electromagnetically transparent transfer plate is disposed above the electromagnetic localization device. An imaging system and a corresponding method for medical imaging make use of such a patient position device.

5 Claims, 3 Drawing Sheets

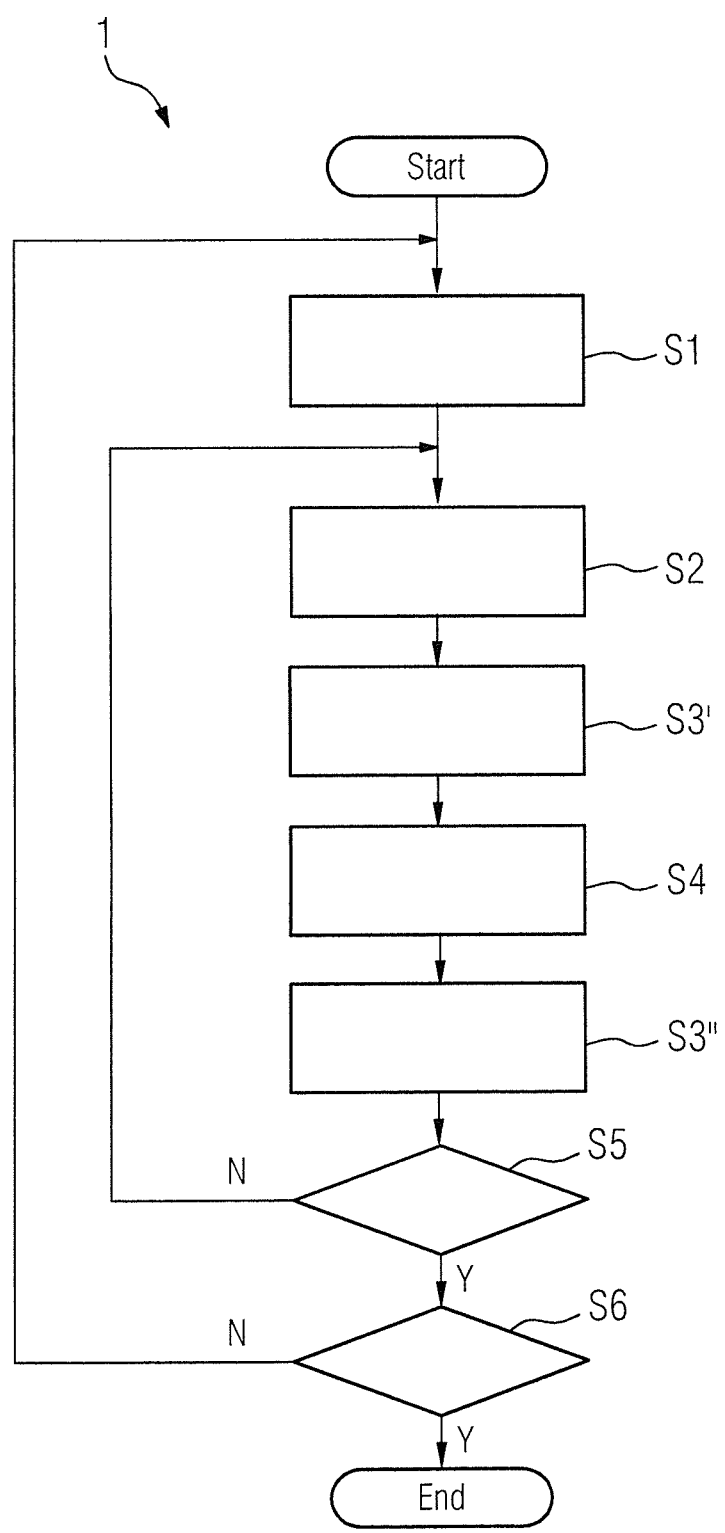

PATIENT POSITIONING DEVICE, AND MEDICAL IMAGING METHOD AND APPARATUS EMPLOYING SAME

BACKGROUND OF THE INVENTION

Field of the Invention

The present invention comprises a patient positioning device, a medical imaging system, and a method for medical imaging.

Description of the Prior Art

In the case of medical needle interventions, such as biopsies, for example, fine needle biopsy, abbreviated FNAB (Fine-needle aspiration biopsy), for acquiring cells from internal organs in diagnoses pertaining to a suspected tumor, or with catheter ablations, image-based navigation support or trajectory planning plays an increasingly important role. In order to depict the structure of tissues and organs in the body of a patient and/or for the spatial imaging thereof, imaging using magnetic resonance tomography (MRT) is an option. A disadvantage with the use of a magnetic resonance tomography apparatus, or a computed tomography (CT) apparatus, the mechanical structure thereof, in which a patient must be conveyed into a tunnel-like opening of the apparatus. It is not possible for a physician to operate in this space. Furthermore, MRT or CT imaging is not possible, or is only possible to a limited extent, due to image artifacts caused by the interaction of the strong static or dynamic electromagnetic fields with the instruments used in a needle intervention, which are generally metallic. For this reason, needle interventions, have conventionally been carried out without MRT or CT imaging, and instead are navigated either without image-based navigation support, i.e. "blind," or modalities are used such as ultrasound or conventional X-ray imaging that, although they do not exhibit the aforementioned disadvantages, depict tissues and organs with lower contrast. Moreover, in the case of X-ray imaging, the patient is subjected to X-ray radiation. Other possibilities for supporting the navigation of a medical needle instrument are markers, positioning aids, camera-based navigation systems and laser systems, which, due to the lack of real-time depiction of the instrument during the intervention, can be used only to a limited extent. Attempts to optimize the mechanical structure of CT or MRT apparatuses, such as by means of a shorter or wider gantry, are only possible to a limited degree, and do not solve the main problem.

A promising approach is the use of a multimodal imaging, in which two or more medical imaging modalities are used. As a result, the advantages and strengths of the respective imaging processes can be combined. Systems are known in which a projection of a spatial image is superimposed over a live screening image, in order to superimpose a representation of tissues having a stronger contrast onto a current image of a medical instrument. Another method is described in the publication by C. Weiss et al., MR-US Fusion for Targeted Prostate Biopsy, 2010 ISMRM (International Society for Magnetic Resonance in Medicine), Annual Meeting, May 1-7, 2010, Stockholm, Sweden. As described herein, a previously acquired MRT image of a volume that includes the prostate of a patient is superimposed on a spatial real-time ultrasound image. The superimposing, or fusing, is achieved using data describing the spatial position of the ultrasound head of the ultrasound apparatus, which are acquired using a position detection system, referred to as a "tracking system". A problem with this method is that when the position of the patient changes after the MRT imaging, it is then difficult, or no longer possible, to fuse the images. This problem arises in particular when the patient is repositioned between the MRT imaging and the ultrasound imaging, or because of movements by the patient, if the ultrasound images are made much later than the MRT images.

SUMMARY OF THE INVENTION

An object of the present invention is to provide a patient positioning device that allows medical imaging of the type described above to be executed in an advantageous manner. Furthermore, it is an object of the invention to provide a corresponding medical imaging system and a corresponding method for medical imaging.

A basis of the invention is a specially designed patient positioning device for medical imaging. The patient positioning device has a transfer plate that is, at least in a region, transparent for electromagnetic radiation, for positioning an examination subject and at least one patient bed. The transfer plate that is transparent for electromagnetic radiation at least in a region thereof, is disposed on the patient bed in order to acquire an image of an examination region of the subject with a first imaging device. Furthermore, in order to acquire the examination region of the subject with a second imaging device, that includes an electromagnetic localization device, the transfer plate located so as to be disposed above the electromagnetic localization device, with the region of the transfer plate that is transparent for electromagnetic radiation can be disposed within the path of the electromagnetic field generated by the electromagnetic localization device.

The patient positioning device for medical imaging in accordance with the invention thus has at least one bed, and a transfer plate. The transfer plate can be disposed on the patient bed or operating table in order to image an examination region of an examination subject, e.g. a human or animal patient, with a first imaging device. As used herein, an examination region can be an organ of the examination subject, which is to be examined for pathological irregularities, by means of a biopsy, for example, or on which surgery is to be performed, e.g. by means of a medical catheter. A transfer plate is to be understood as a plate for supporting and/or positioning the examination subject. The transfer plate can be, or is, disposed in a fixed manner on a patient bed, or can be exchanged between different patient positioning devices and/or patient beds. As an example, the patient can first be moved, while lying on the transfer plate on a patient positioning device in order to acquire a magnetic resonance image of the examination region, and subsequently, together with the transfer plate, can be moved to an operating table for surgery. For the magnetic resonance examination, the patient, lying on the transfer plate, is conveyed, together with the transfer plate and the patient bed, into an examination room in which the magnetic resonance apparatus is installed. For this purpose, the transfer plate is disposed in a locked position in relation to the patient bed. The patient bed is preferably designed to be mobile, such as on wheels. A design similar to a robot arm is also conceivable.

The transfer plate can then be disposed for imaging the examination region of the examination subject with a second imaging device. The second imaging device includes an electromagnetic localization device, and the transfer plate can be disposed above this electromagnetic localization device. The region of the transfer plate that is transparent for electromagnetic radiation is disposed above and in the electromagnetic field generated by the electromagnetic localization device. It is also possible for the entire transfer plate to be designed to be transparent for electromagnetic radiation.

The region that is transparent for electromagnetic radiation is understood to be a region through which electromagnetic waves, i.e. waves having oscillating electrical and magnetic fields, can pass without difficulty, i.e. without substantial interaction with the matter of the region. Because the interaction of electromagnetic waves with matter is highly dependent on the frequency of the waves, the material of the region of the transfer plate that is transparent for electromagnetic radiation is coordinated to wavelengths of the electromagnetic localization device. These can be derived, for example, from a data sheet for the electromagnetic localization device. A region that is electromagnetically transparent, that exhibits a pre-definable damping, is also conceivable. The degree of damping can be pre-defined, for example, in accordance with the electromagnetic localization device that is used. By means of the electromagnetically transparent region of the transfer plate, which can be disposed, according to the invention, above the electromagnetic localization device, i.e. between the electromagnetic localization device and the examination region of the examination subject, it is possible to record the examination region of the examination subject with the second imaging device, incorporating the electromagnetic localization device.

A localization device is generally understood to be a device that enables the identification of the position of an object, wherein the localization includes the determination of a location coordinate for a given point on the object, and the spatial orientation of the object. In conjunction with the fundamental concept according to the invention, the localization device serves to locate a component of the second imaging device, such as an image sensor, for example. Electromagnetic localization devices are known in the prior art. In one design, one or more coils can be disposed on the tip of, for example, an endoscopic instrument, in which a voltage is induced by an electromagnetic field that is generated outside of the patient, and measurement of the induced voltages produced by the respective coils enables the determination of the position and location of the endoscopic instrument. A system of this type is commercially available, for example, from the company Northern Digital Incorporated, NDI, as a product called "Aurora."

In another design, a high-frequency transponder is located on the tip of an endoscopic instrument, a so-called RFID (Radio Frequency Identification) tag. The determination of the position of a radio-frequency transponder using a phase-sensitive evaluation of the received signal is known form DE 10 2006 029 122 A1. The antennas for the transponders are excited by means of the radio-frequency field, and supply the transponders with electric energy. The transponders transmit a localization signal, which is received in a phase-sensitive manner by numerous receivers. According to the method described in greater detail in DE 10 2006 029 122 A1, the precise location of each transponder is determined.

In a further embodiment, the first imaging device can be a computed tomography apparatus or a magnetic resonance tomography apparatus, or a C-arm X-ray apparatus. The second imaging device can be a sonography device having a transducer, wherein the electromagnetic localization device is designed for locating the transducer.

Sonography, echography, or colloquially, ultrasound, is the use of ultrasound as an imaging modality in medical practice for the examination of, for example, organic tissues. A substantial advantage of sonography is that the sound waves that are used are innocuous, so that imaging can be carried out over longer periods of time, e.g. as live-imaging, without exposing the subject to radiation. Typically, a sonography apparatus has an electronic circuitry for generating the sound and for processing the image data, and an interface for transmitting the image data to a control computer. Normally, a transducer or an ultrasound probe is connected by means of a cable to the electronic circuitry of the sonography apparatus, such that it can move freely. In recent years, so-called three-dimensional sonography has been used with increasing frequency. For this purpose, the transducer is panned over an examination region, and the images acquired in this manner are converted to a three-dimensional image. A three-dimensional depiction in real-time is also possible. It is important to determine the angle between the transducer and a pre-defined plane, the so called surface scan angle, and to take this into account in the computing of the three-dimensional ultrasound image. Another possibility is to use a two-dimensional configuration of ultrasound transducers in a so-called phased array, in which the panning of the beam is not carried out mechanically, but rather electronically.

Advantages with the use of a magnetic tomography apparatus as the first imaging device have already been described. In particular, with the use of a sonography apparatus, having a transducer as the second imaging device, and the localization of the transducer with the electromagnetic localization device, the execution of the method described in the publication by C. Weiss et al., MR-US Fusion for Targeted Prostate Biopsy, 2010 ISMRM (International Society for Magnetic Resonance in Medicine), Annual Meeting, May 1-7, 2010, Stockholm, Sweden, is simplified.

In another embodiment, the patient positioning device includes the aforementioned transfer plate and the patient bed for imaging the examination region of the examination subject with the second imaging device. A cavity for accommodating the electromagnetic localization device is formed in at least the region between the electromagnetically transparent region of the transfer plate and the patient bed, wherein the regionally electromagnetically transparent transfer plate is disposed on the first patient bed.

This embodiment thus includes a patient bed for imaging with both the first as well as the second imaging devices. The examination subject is positioned on the transfer plate for imaging with the first imaging device, and an image of the examination region is acquired. Subsequently, the examination subject, lying on the transfer plate, can be moved out of the first imaging device, and images can be acquired with the second imaging device. The imaging process for the second imaging device uses an electromagnetic localization device, which can be disposed between the transfer plate and the examination region of the examination subject. In order to dispose the electromagnetic localization device in such a manner, a cavity is provided for accommodating the electromagnetic localization device that is formed between the region of the transfer plate that is transparent for electromagnetic radiation and the first patient bed. The cavity can be formed, for example, by the transfer plate being at a spacing from the patient bed, by means of which an intermediate space is formed in which the electromagnetic localization device can be inserted. An advantage obtained with this feature is that only one patient bed is required for imaging with both the first and the second imaging device. The electromagnetic localization device can be removed for imaging with the first imaging device, such that no feedback effects occur in the imaging.

In an alternative embodiment of the patient positioning device according to the invention, the patient bed is a first patient bed and the patient positioning device includes the aforementioned regionally electromagnetically transparent transfer plate, and a second patient bed for imaging the examination region of the examination subject. The regionally electromagnetically transparent transfer plate can be disposed on the second patient bed, and the electromagnetic localization device can be disposed on the second patient bed and under the part of the transfer plate that is transparent for electromagnetic radiation.

In this embodiment, two different patient beds are used. The examination subject is placed on the transfer plate for imaging with the first imaging device, and an image of the examination region is acquired. Subsequently, the examination subject, lying on the transfer plate, is moved from the first bed to the second patient bed. The imaging process for the second imaging device uses an electromagnetic localization device, which can be disposed, or is disposed, on the second patient bed. When the examination subject lying on the transfer plate is placed on the second patient bed, at least the electromagnetically transparent region of the transfer plate is disposed between the examination region of the examination subject and the electromagnetic localization device, and images can be acquired with the second imaging device using the electromagnetic localization device. An advantage obtained with this feature is that the two patient beds can be individually designed, in terms of their geometries, for example, for the respective imaging processes.

Another fundamental concept of the invention concerns a medical imaging system for recording an examination region of an examination subject. The medical imaging system has a first imaging device, a second imaging device that includes an electromagnetic localization device, a transfer plate, which is at least in part transparent for electromagnetic radiation, for positioning the examination subject, at least one patient bed, a computing and control unit, and a display unit. The transfer plate that is electromagnetically transparent in a region thereof can be disposed on the patient bed for imaging the examination region of the examination subject with the first imaging device. The regionally electromagnetically transparent transfer plate can be disposed above the electromagnetic localization device for recording the examination region of the examination subject with the second imaging device, and the electromagnetically transparent region can be disposed above and in the path of the electromagnetic field generated by the electromagnetic localization device. The computing and control unit is designed to receive images from the first imaging device and the second imaging device, and to display at least one of the images on the display unit.

The basic concept of the medical imaging system according to the invention for recording an examination region of an examination subject is the use of two imaging devices, wherein the second imaging device includes an electromagnetic localization device, together with the use of the transfer plate, that has a region that is transparent for electromagnetic radiation, independently of the wavelengths that are used in the electromagnetic localization device, and is designed for positioning the examination subject on the at least one patient bed. The examination subject can be placed on the transfer plate, and can be disposed on the first patient bed for imaging the examination region of the examination subject with the first imaging device. The transfer plate, together with the examination subject placed thereon, can be disposed above the electromagnetic localization device for imaging the examination region of the examination subject with the second imaging device, with the electromagnetically transparent region of the transfer plate disposed above and in the field of the electromagnetic localization device. The computing and control unit, e.g. a computer, is designed to receive images from the first imaging device and the second imaging device, and to display at least one of the images on the display unit, e.g. a computer monitor. For this purpose, the two imaging devices can be connected to the computing and control unit by a suitable communication path, e.g. a data cable, and the computing and control unit can execute a computer program that which enables the reception and depiction of the image or images.

In an embodiment, the first imaging device can be a computed tomography apparatus or a magnetic resonance tomography apparatus, or a C-arm X-ray apparatus. The second imaging device is a sonography apparatus with a transducer, wherein the electromagnetic localization device is designed for localizing the transducer.

Contemporary computed tomography apparatuses, magnetic resonance tomography apparatuses, C-arm X-ray apparatuses and sonography apparatuses usually have interfaces for making images accessible to a computing and control unit, e.g. a computer, such that the receiving of images is possible without significant effort.

Preferably the computing and control unit is designed for superimposing an image from the first imaging device and an image from the second imaging device, to form a superimposed image, and to display the superimposed image on the display unit.

The location-specific superimposing of two images from two different imaging devices is also referred to as image fusion. Methods are known for this purpose, in particular from the field of medical image processing. One of the described medical imaging systems for recording an examination region of an examination subject is particularly suited for image fusion, because it can be ensured that the position of the examination subject during the recording with both imaging devices does not change. This is achieved because the examination subject positioned on the same transfer plate for imaging with both imaging devices, and because the moving of the examination subject from the first imaging device to the second imaging device can be executed quickly. The computing and control unit can, by means of a computer program, be programmed to superimpose two received images and to depict the superimposed images on the display unit, for example. Localization data from the electromagnetic localization device can be included in the fusion of the two images. The electromagnetic localization device supplies data, in one embodiment, regarding the location vector and regarding the orientation of a transducer of a sonography apparatus. This data makes it easier to fuse a sonographic image with a spatial image, e.g. a magnetic resonance tomography image.

The invention also encompasses a method for medical imaging with a medical imaging system for acquiring an examination region of an examination subject. The medical imaging system has a first imaging device, and a second imaging device, that includes an electromagnetic localization device. Furthermore, the medical imaging system has a transfer plate that is, at least in regions, transparent for electromagnetic radiation, for positioning the examination subject, at least one first patient bed, a computing and control means, and a display means. The method for medical imaging with the medical imaging system includes at least the following steps:

S1) positioning the examination subject on the transfer plate that is, at least in regions, transparent for electromagnetic radiation, disposing the, at least in regions, electromagnetically transparent transfer plate on a patient bed, recording of a first image of the examination region of the examination subject with the first imaging device, and supplying the first image to a computing and control means;

S2) disposing the regionally electromagnetically transparent transfer plate above the electromagnetic localization device, with the electromagnetically transparent region of the transfer plate above the electromagnetic localization device, acquiring a second image of the examination region of the examination subject with the second imaging device, and supplying the second image to the computing and control unit;

S3) receiving at least one of the supplied images at the computing and control unit and displaying at least one image on the display unit.

Advantageously, the method according to the invention is executed, at least in part, by a computer program, for example, which is installed in the computing and control unit.

It has been shown to be advantageous for at least one step to be repeated.

It is possible, for example, to repeat steps S2 and S3. This means that the examination region of the examination subject is acquired repeatedly using the second imaging device, and the control and computing unit receives the respective last image and displays it on the display means. Preferably, the procedure is repeated until a stopping criterion has been met. A stopping criterion can be, for example, the actuation of a button, the acquisition of a given number of repetitions, or reaching a given time.

It is advantageous for the method to be executed, at least in part, automatically.

For example, after receiving an image, the image can be automatically displayed on the display unit by means of the computing and control unit.

BRIEF DESCRIPTION OF THE DRAWINGS

FIG. 5 is a flowchart of an embodiment of the method according to the invention for medical imaging with a medical imaging system for imaging an examination region of an examination subject.

DESCRIPTION OF THE PREFERRED EMBODIMENTS

Figure 1:
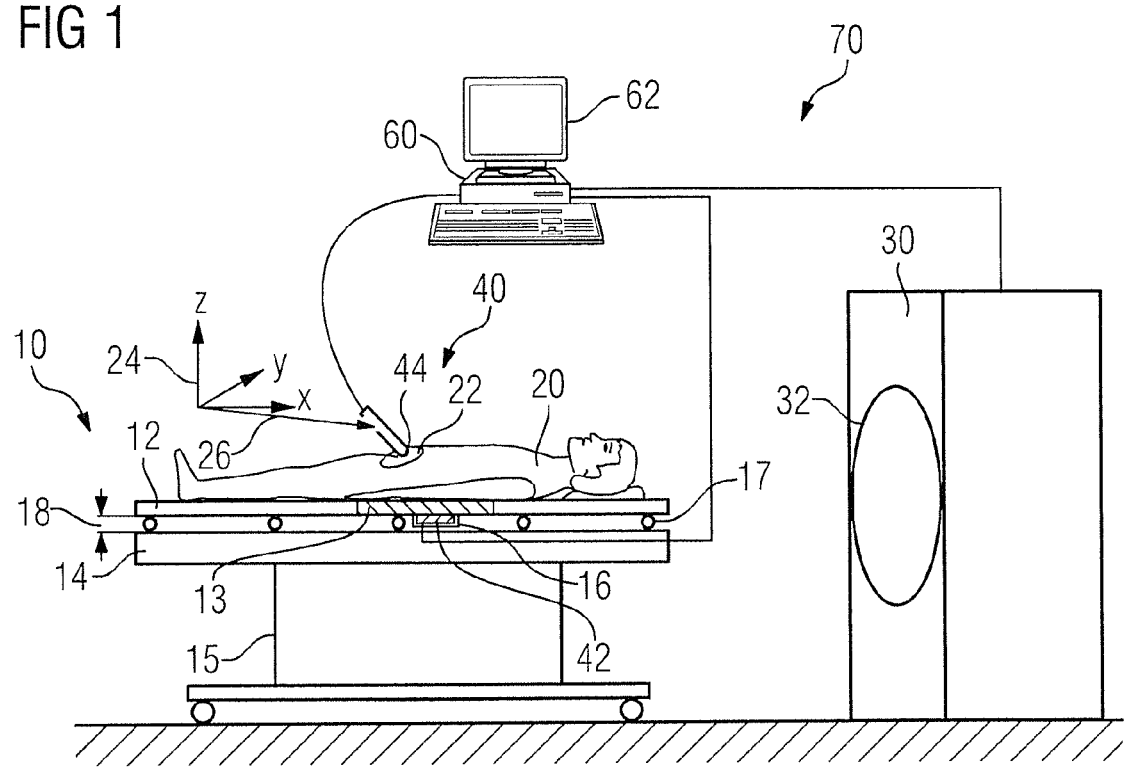
FIG. 1 schematically shows an embodiment of a medical imaging system for imaging an examination region of an examination subject according to the invention.

FIG. 1 schematically shows an embodiment of a medical imaging system 70 for recording an examination region 22, here the prostate, of an examination subject 20, here a human patient. The medical imaging system 70 has a first imaging device 30, here a magnetic resonance tomography apparatus, a second imaging device 40, here a sonography apparatus with a transducer 44. The second imaging device 40 has an electromagnetic localization device 42. Furthermore, the medical imaging system 70 has a patient positioning device 10 that has a transfer plate 12, which is transparent for electromagnetic radiation in a region 13, for positioning the examination subject 20, and a first patient bed 14. The medical imaging system 70 further has a computing and control unit 60, here a computer, and a display unit 62, here a computer monitor. The transfer plate 12 that is transparent for electromagnetic radiation in the region 13, can be disposed with the first imaging device 30 on the first patient bed 14 for imaging the examination region 22 of the examination subject 20 with the first imaging device 30. The first patient bed 14 has a stand or base 15 mounted on a platform with rollers, by means of which the patient bed 15, with the transfer plate 12 and the examination subject 20, can be moved into the first imaging device 30, the magnetic resonance tomography apparatus with a gantry 32, for recording the examination region 22. Furthermore, the transfer plate 12 can be disposed above the electromagnetic localization device 42 for imaging the examination region 22 of the examination subject 20 with the second imaging device 40, and the electromagnetically transparent region 13 can be disposed above the electromagnetic localization device 42. The patient bed 14 is designed for imaging with both the first imaging device 30 as well as the second imaging device 40. After recording the examination region 22 of the examination subject 20 with the first imaging device, the examination subject 20, lying on the transfer plate 12, can be removed from the first imaging device 30 and images can be acquired with the second imaging device 40. The imaging method for the second imaging device 40 uses the electromagnetic localization device 42, which can be disposed between the transfer plate 12 and the examination region 22 of the examination subject 20. In order to position the electromagnetic localization device 42, a cavity 16 for accommodating the electromagnetic localization device 42 is formed between the electromagnetically transparent region 13 of the transfer plate 12 and the first patient bed 14. The cavity 16 can be formed, for example, in that the transfer plate 12 is spaced apart from the first patient bed 14, by means of rollers 17, for example, by means of which an intermediate space 18 is formed, in which the electromagnetic localization device 42 can be inserted. An advantage obtained with this feature is that only one patient bed is needed for recording with the first and the second imaging devices. The electromagnetic localization device 42 can be removed for recording with the first imaging device 30, such that no feedback effects occur in the imaging. The localization device 42 enables the determination of a location coordinate for a given point of the transducer 44 of the second imaging device 40, here the sonography apparatus, depicted as a location vector 26 of a Cartesian coordinate system 24, and the spatial orientation of the transducer 44, not shown in FIG. 1. The computing and control unit 60 is designed to receive images from the first imaging device 30 and the second imaging device 40, by data lines, for example, and to display at least one of the images on the display unit 62. Through the localization of the transducer 44, i.e. the known location coordinate and the known spatial orientation of the transducer 44, images from the second imaging device 40 are particularly suited for image fusion with an image from the first imaging device 30. Advantageously, localization data from the electromagnetic localization device 42 are included in the fusion of the two images. These data make it easier to fuse the sonographic images with a spatial image, e.g. a magnetic resonance tomographic image. The computing and control unit 60 can be designed, for example, to be capable of superimposing two received images, by means of a computer program, for example, and depicting the superimposed images on the display unit 62.

Figure 2:
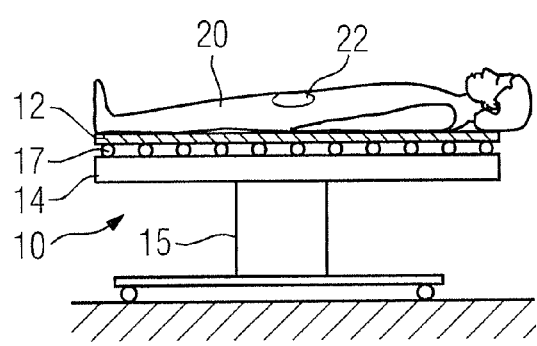
FIG. 2 schematically shows an embodiment of a patient positioning device in a first state.
Figure 3:
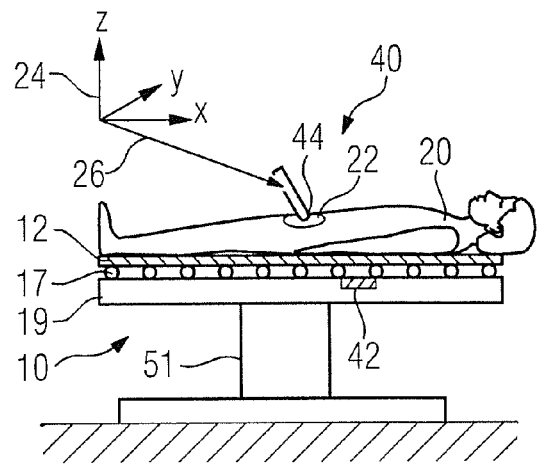
FIG. 3 schematically shows the embodiment of a patient positioning device of FIG. 2 in a second state.
Figure 4:
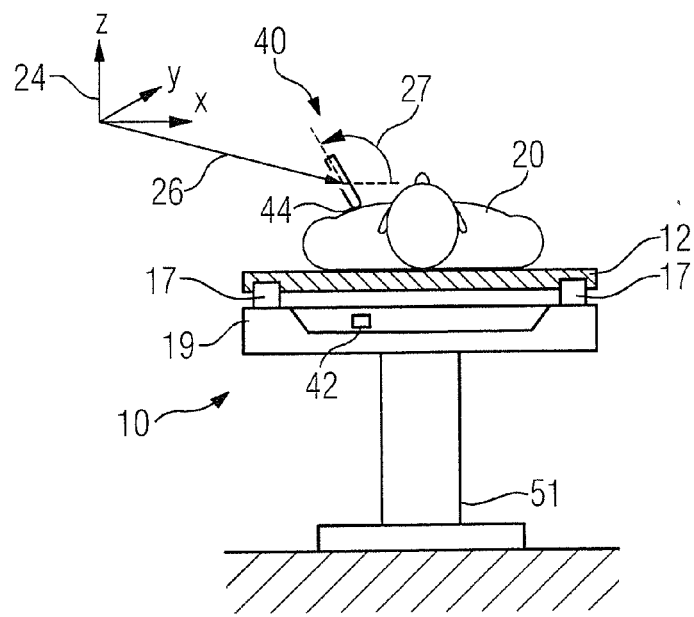
FIG. 4 schematically shows the embodiment of a patient positioning device of FIG. 3 in the second state, in a top view.

An embodiment of a patient positioning device 10 in a first state is depicted schematically in FIG. 2, and another state is illustrated in FIG. 3. In this embodiment example, two different patient beds are used. An examination subject 20, here a human patient, is positioned on a transfer plate 12 for recording an examination region 22, here a prostate gland, with a first, not shown, imaging device. The transfer plate 12 is disposed on a first patient bed 14 for this purpose, which in turn is disposed on a stand 15. Subsequently, the examination subject 22, remaining on the transfer plate 12, can be slid, by means of rollers 17, from the first patient bed 14 to a second patient bed.

FIG. 3 shows, schematically, the embodiment example of a patient positioning device 10 from FIG. 2 in a second state. The examination subject 20, i.e. the human patient, who continues to remain on the transfer plate 12, is pushed onto a second patient bed 19, here an operating table with a stationary stand 51, by means of rollers 17, in a second state. The imaging process for a second imaging device 40, here a sonography apparatus with a transducer 44, uses an electromagnetic localization device 42, which is disposed on the second patient bed 19 integrated, in this case, in the second patient bed 19. Because the entire transfer plate 12 consists of an electromagnetically transparent material, an electromagnetically transparent region of the transfer plate 12 is also disposed between an examination region 22, here the prostate, of the examination subject 20 and the electromagnetic localization device 42, and images can be acquired with the second imaging device 40, using the electromagnetic localization device 42, which determines a location vector 26 of a Cartesian coordinate system 24. The electromagnetic transparency is in a wavelength range used by the electromagnetic localization device 42. An advantage obtained from the use of two patient beds is that the two patient beds can be designed particularly well for the respective imaging procedures, through their geometric design, for example.

The embodiment example of a patient positioning device 10 from FIG. 3 in the second state is shown schematically in a top view. It shows the examination subject 20, here the human patient, which, lying on a transfer plate 12, is conveyed by means of rollers 17 to a second patient bed 19, here the operating table with a stationary stand 51. In this state, an examination region (not shown) of the examination subject 20 can be imaged with a second imaging device 40, here a sonography apparatus with a transducer 44. An electromagnetic localization device 42 is integrated in the second patient bed 19. This electromagnetic localization device 42 enables the determination of a location vector 26 from the origin of a Cartesian coordinate system 24 to a given point of the transducer 44, as well as the determination of a surface scanning angle 27, i.e. an angle between the transducer and a given plane of the Cartesian coordinate system 24.

Lastly, FIG. 5 shows an exemplary flow chart for the method 1 according to the invention for medical imaging with a medical imaging system, for imaging an examination region of an examination subject. The medical imaging system comprises thereby, a first imaging device and a second imaging device, which comprises an electromagnetic localization device. Furthermore, the medical imaging system has a transfer plate, which is, at least in regions, transparent for electromagnetic radiation, for positioning the examination subject, at least one first patient bed, a computing and control means, and a display means. The method 1 includes the steps S1, S2, S4-S6, as well as S3' and S3". Step 1 is the "start," and it finishes at "end" after completing step S6. The individual steps are:

S1) positioning the examination subject on the transfer plate, which is, at least in regions, transparent for electromagnetic radiation, positioning the at least in regions electromagnetically transparent transfer plate on the first patient bed, recording of a first image of the examination region of the examination subject with the first imaging device and supplying the first image to the computing and control unit;

S2) positioning the at least in regions, electromagnetically transparent transfer plate above the electromagnetic localization device, wherein the electromagnetically transparent region of the transfer plate is disposed above the electromagnetic localization device, recording a second image of the examination region of the examination subject with the second imaging device and supplying the second image to the computing and control means;

S3') receiving the images supplied by the computing and control unit;

S4) location specific superimposing of the image from the first imaging device with the image from the second imaging device, to form a superimposed image;

S3") displaying the superimposed image on a display means;

S5) querying of a first stopping criterion, and if the stopping criterion is met, jumping to step S6, otherwise jumping to step S2;

S6) querying a second stopping criterion, and if the second stopping criterion is met, finishing the method, "end," otherwise jumping to step S1.

A first stopping criterion can, for example, be understood to be the actuation of a first button. If the button is not actuated, the stopping criterion is not met and the method jumps to step S2, in which another image of the examination region of the examination subject is recorded with the second imaging device, and supplied to the computing and control means. If the first button is actuated, and the first stopping criterion is thus met, then a second stopping criterion, such as the actuation of a second button, for example, is checked. If the second button is not actuated, the second stopping criterion is not met, and the method jumps to step S1, in which another image of the examination region of the examination subject is recorded with the first imaging device, and supplied to the computing and control means. If the second stopping criterion is met, the method is completed.

With the imaging method in which the ultrasound image is registered with a previously recorded spatial image, the efficient positioning of a patient from the first imaging device to the ultrasound apparatus, which comprises an electromagnetic localization device, is essential. Thus, a patient positioning device is proposed, by means of which the patient does not need to be relocated. The patient is positioned in a stationary manner on an electromagnetically transparent transfer plate according to the invention, which can be disposed on an MRT or CT patient bed. There is either a cavity between the transfer plate and the patient bed, in which the electromagnetic localization device can be inserted, when the patient is outside of the MRT or CT apparatus, or the transfer plate is pushed onto a second patient bed, on which the electromagnetic localization device is disposed. An electromagnetically transparent transfer plate also has a positive effect on the magnetic resonance imaging. It is also conceivable for one or both of the patient beds to be designed to be moveable, by means of rollers, in the manner of a trolley, in order to be able to leave the room in which the MRT or CT apparatus is located following the MRT or CT recording, in order to free the room for other patients. Thus, the following cases are conceivable:

an MRT or CT patient bed that can roll exhibits an intermediate space between the transfer plate and the patient bed. An MRT image is acquired, the patient is conveyed out of the MRT room and the electromagnetic localization device is inserted in the intermediate space;

the transfer plate is pushed from the MRT or CT patient bed onto a second patient bed that can roll, after an MRT or CT recording, which exhibits an intermediate space between the transfer plate and the patient bed. The patient is conveyed out of the MRT room and the electromagnetic localization device is inserted in the intermediate space;

the MRT or CT patient bed does not exhibit an intermediate space between the transfer plate and the patient bed. Following an MRT or CT recording, the patient is conveyed out of the MRT room and the transfer plate is pushed onto a second patient bed, on which the electromagnetic localization device is disposed;

following an MRT or CT recording, the patient is not conveyed out of the MRT room. Instead, the electromagnetic localization device is inserted in the intermediate space between the transfer plate and the MRT or CT patient bed, or the transfer plate is pushed onto a second patient bed, on which the electromagnetic localization device is disposed. As a result of the recordings with the ultrasound apparatus being carried out in the MRT or CT examination room, it is possible, if desired, to quickly acquire additional MRT or CT recordings, or the MRT apparatus can be used for other purposes, such as a temperature monitoring.

Although modifications and changes may be suggested by those skilled in the art, it is the intention of the inventor to embody within the patent warranted hereon all changes and modifications as reasonably and properly come within the scope of his contribution to the art.

I claim as my invention:

1. A medical imaging method for obtaining medical images of an examination subject with a first medical imaging device comprising a magnetic resonance imaging apparatus and with a second medical imaging device that comprises an electromagnetic localization device that emits electromagnetic radiation, said method comprising:

placing a patient on a single transfer plate, said single transfer plate comprising at least one transparent region in which said single transfer plate is transparent to said electromagnetic radiation;

supporting said single transfer plate on one patient support, with said one patient support and said single transfer plate thereby forming a single combined supporting structure for said patient, with said electromagnetic localization device being selectively removable from said single combined supporting structure;

selectively mechanically configuring said single combined supporting structure to a first state, in which said electromagnetic localization device is not present in said single combined supporting structure;

operating said first medical imaging device to obtain a magnetic resonance image, as a first medical image, of an examination region of the examination subject on the single transfer plate with said single combined supporting structure in said first state;

selectively mechanically configuring said single combined supporting structure to a second state in which said electromagnetic localization device is present in said single combined supporting structure; and operating said second medical imaging device to obtain a second medical image of said examination region while said examination subject is on said transfer plate with said single combined supporting structure in said second state, with said single transfer plate being positioned on said one patient support with said at least one transparent region disposed over said electromagnetic localization device.

2. A medical imaging method as claimed in claim 1 wherein said second medical imaging device is a sonography apparatus comprising a movable applicator to expose the examination subject to a sonographic field, and wherein said electromagnetic localization device is configured to localize said applicator.

3. A medical imaging method as claimed in claim 1, wherein said method further comprises, using a computerized control unit, superimposing said first medical image and said second medical image on a display unit in communication with said computerized control unit.

4. A medical imaging method as claimed in claim 1 wherein said one patient support is configured to allow movement of said single transfer plate thereon in order to position said at least one transparent region over said electromagnetic localization device.

5. A medical imaging method as claimed in claim 1 wherein said single combined supporting structure comprises a surface with supporting elements on said surface on which said single transfer plate is supported, with a spacing between said surface and said single transfer plate, and wherein said single supporting structure further comprises a receptacle within said spacing in which said electromagnetic localization device is removably inserted, with said single combined supporting structure being selectively mechanically configurable between said first state and said second state by said receptacle being empty in said first state and by said electromagnetic localization device being inserted in said receptacle in said second state.

* * * * *